United States Patent [19]  [11] 4,116,983
Schmidt  [45] Sep. 26, 1978

[54] TWO STAGE MALEIC ANHYDRIDE PROCESS

[75] Inventor: John P. Schmidt, Princeton, N.J.

[73] Assignee: Halcon International, Inc., New York, N.Y.

[21] Appl. No.: 800,141

[22] Filed: May 24, 1977

Related U.S. Application Data

[63] Continuation of Ser. No. 408,344, Oct. 23, 1973, abandoned.

[51] Int. Cl.$^2$ ............................................. C07D 307/60
[52] U.S. Cl. ................................................. 260/346.75
[58] Field of Search ........................ 260/346.8, 346.75

[56] References Cited

U.S. PATENT DOCUMENTS

| 2,605,238 | 7/1952 | Krantz | 260/346.75 |
| 3,247,279 | 4/1966 | Lidov | 260/346.75 |
| 3,759,840 | 9/1973 | Barker | 260/346.75 |

Primary Examiner—Henry R. Jiles
Assistant Examiner—Bernard Dentz
Attorney, Agent, or Firm—William C. Long; David Dick; Riggs T. Stewart

[57] ABSTRACT

Benzene is oxidized with air to produce maleic anhydride in catalyst-containing reactors arranged in series, the gaseous effluent from the first reactor being passed to the second reactor after introduction of substantial amounts of benzene.

4 Claims, No Drawings

TWO STAGE MALEIC ANHYDRIDE PROCESS

This is a continuation of application Ser. No. 408,344 filed Oct. 23, 1973 and now abandoned.

The invention relates to the catalytic oxidation of benzene and is more particularly concerned with the preparation of maleic anhydride by such oxidation.

The production of maleic anhydride by the partial oxidation of benzene in a vapor-phase system using a contact catalyst involves a well-known reaction and has been prracticed commercially for many years. Thus, a typical commercial process involves passing a mixture of air and benzene in vapor form containing about 1 to 2 mol percent of benzene over a catalyst disposed in tubes arranged in a reactor vessel commonly referred to as a converter. The tubes are surrounded by a heat transfer liquid bath, e.g. salt. Following catalyst reaction, the hot gaseous effluent from the converter is suitably treated to recover the maleic andydride. Typically, the effluent is cooled to condense a portion of the maleic anhydride contained in it which is accumulated in a crude maleic anhydride storage unit. The cooled gaseous stream from which a portion of the maleic anhydride has thus been condensed, and contained residual maleic anhydride vapor, is passed to a scrubbing zone, where it is contacted with a scrubbing liquid, usually water, so that the maleic anhydride entrained in the gaseous stream is extracted by the water, forming an aqueous maleic acid solution. The maleic acid solution is then sent to a dehydration zone for removal of water and conversion of the maleic acid to maleic anhydride. The dehydration treatment is most advantageously carried out in the presence of an organic water-entraining agent, such as xylene or toluene, which, forming an axeotrope with the water, aids in its removel. The maleic acid solution is heated in the dehydration zone to an elevated temperature, and the water and azeotroping agent are vaporized away from the maleic anhydride which is produced. The maleic anhydride thus obtained is recovered from the dehydration zone and then is sent to a crude maleic anhydride storage unit where it is combined with the condensed maleic anhydride previously obtained. Customarily, the combined crude maleic anhydride thus obtained is next subjected to a purification treatment involving the removal of remaining azeotropic agent and distilation of crude maleic anhydride to produce substantially pure product.

It will, of course, be apparent that one objective of those charged with the commercial production of maleic anhydride is to achieve the maximum yield of product from the benzene employed. This involves consideration of conversion and selectivity in the oxidation portion of the process. An equally important objective is to increase the productivity of a given commercial unit i.e. to produce the maximum amount of maleic anhydride from a plant of a given size involving a given capital investment. In the usual commercial process of the character just described, catalysts are commonly used which are based upon a combination of vanadium and molybdenum in oxidized form. In the usual case, the vanadium and molybdenum oxides have been combined with the oxidized forms of one or more other metals of various types. The use of highly active catalysts makes it possible to increase conversion of benzene and selectivity to the desired maleic anhydride. The process is nevertheless limited since the mixtures of oxygen-containing gas and benzene must be relatively dilute with respect to benzene in order to lessen flammability problems. A somewhat similar situation exists in connection with the catalytic oxidation of naphthalene to produce phthalic anhydride and, as a result, various efforts have been made to increase the producitvity of a given phthalic anhydride plant while observing the limitations in the hydrocarbon concentration of the gases present at any particular point in the oxidation section of the plant. In this connection, it has been proposed to carry out the oxidation in a series of catalyst chambers with the effluent from one chamber being passed into the inlet of the next succeeding chamber until the hydrocarbon has been substantially exhausted. Such operation, however, is not entirely satisfactory and various proposals for improving it have been put forth such as those found in Benichou et al. U.S. Pat. Nos. 3,072,682 and 3,180,877. In these two disclosures emphasis is placed on injecting water and air into the gaseous effluent. British Pat. No. 790,559 proposes spaced injections of reactant in a single reactor but illustrates this technique only in the oxidation of crotonaldehyde, butylene glycol and n-butanol. Such a process involves serious practical problems when applied to large-scale benzene oxidation. The oxidation of benzene, while similar in some aspects to the oxidation of other compounds, involves important differences and considerations and these prior proposals do not provide an effective solution to the problem of increasing plant productivity in the field of benzene oxidation.

It is accordingly an object of the present invention to provide an improved process for the preparation of maleic anhydride by the catalytic oxidation of benzene.

It is a further object of the invention to provide an improved process of the character indicated which makes possible substantially increased plant productivity.

It is still a further object of the invention to accomplish the foregoing objects while maintaining high conversions, selectivities, and yields.

In accordance with the invention, benzene is oxidized with molecular oxygen in a dilute state by bringing a mixture of vaporized benzene and air of controlled benzene content into the presence of a contact catalyst comprising vanadium and molybdenum in a first oxidation zone under controlled pressure and temperature conditions, passing the gaseous effluent from the first oxidation zone into a second oxidation zone substantially at a temperature at least as great as the temperature in the first oxidation zone while introducing a controlled amount of benzene into the gaseous effluent from the first oxidation zone prior to its introduction into the second oxidation zone, and bringing the thus benzene-enriched mixture into contact with a catalyst comprising vanadium and molybdenum disposed in the second zone.

It has been found that, in the case of the oxidation of benzene to maleic anhydride, it is necessary to operate under conditions maintained within relatively narrow ranges and while using air-benzene mixtures containing selected quantities of vaporized benzene. Thus, the amount of benzene in the feed to the first reactor is in the range of about 1 to 2 mol percent, preferably 1.2 to 1.8 mol percent while the vapor feed to the second reactor contains about 0.8 to 1.8 mol percent of benzene, preferably 1.0 to 1.6 mol percent, the total not being reater than 3.8, preferably not greater than 3.4. The benzene content to the second reactor is, of course, the sum of the unreacted benzene in the effluent from the first reactor plus fresh benzene injected into the effluent prior to its introduction into the second reactor. In addition, the ratio of the benzene content of the feeds to the first reactor and to the second reactor preferably lies in the range of 1.8 to 0.6.

As previously mentioned, the temperature in the second oxidation zone is substantially at least as great as the temperature in the first oxidation zone, but the temperature in the second oxidation zone may be somewhat higher if desired e.g. up to 30° C. higher. In any case, the temperature in the first oxidation zone will lie within the range of 330° to 425° C. preferably 330° to 400° C. and the temperature in the second oxidation zone will lie within the range of 330° to 425° C. preferably 330° to 400° C. In the foregoing discussion of temperatures, each temperature referred to is the temperature of the salt bath surrounding the catalyst tubes and maintained under constant circulation. The maintenance of the salt bath at the desired temperature is achieved by appropriate heat exchange in the salt circuit as is well known to persons skilled in the art. Ordinarily, each reactor is provided with a single salt circuit, each maintained at the desired temperature. The flow of salt in the circuit is maintained at a rate such that the above-specified temperature values are achieved and it has been found that the average temperature of the gases flowing through the reactor is not substantially different from the temperature of the associated salt bath except, of course, for the conventional "hot spots" which may be significantly higher, e.g. 30°–50° C. higher.

In accordance with one embodiment of the invention, the second reactor may be provided with two independent salt circuits axially spaced along the reactor tubes so that two different temperature zones may be provided in the second reactor i.e., a first temperature zone extending from the inlet of the second reactor to any desired downstream point and a second temperature zone extending from that point to the outlet of the reactor. Ordinarily, the entire second reactor has a single salt circuit maintained at the operating temperature, but it may be desired to have the downstream portion of the second reactor, i.e. the portion containing the second salt bath, at a higher temperature than the upstream portion, although this temperature difference will ordinarily not exceed about 30° C. As a rule, the first and second salt baths extend over at least one-fourth of the length of the catalyst-containing tubes. Generally the catalyst beds in the two reactors are of substantially equal height and diameter and this is preferred to give optimum results. However, the catalyst beds of one reactor can differ in size from the catalyst beds in the other reactor so long as they make possible the maintenance of the desired space velocity through both reactors. In passing from the first reactor to the second reactor, it is necessary to introduce only benzene into the gas stream. If it is desired to cool the stream to minimize flammability problems, this can be done by simple indirect heat exchange, but such cooling is preferably held to a minimum and is not essential from a process standpoint.

The pressure of the gaseous feed to the first oxidation zone is maintained at a value of 10 to 60 psig with the pressure gradually dropping as the gaseous mixture passes through the oxidation zones and any intermediate equipment to a final outlet pressure in the range of 0 to 50 psig. Preferably, the pressure at the feed of the first reactor is 20 to 30 psig and the pressure at the outlet of the second reactor is 20 to 5 psig. The space velocity of the gaseous mixture through the reactors is also maintained within specified limits. Ordinarily, the space velocity (standard conditions) is 1800 to 3500 hr.$^{-1}$, preferably 2000 to 3100 hr.$^{-1}$. One of the aspects of the process of the invention is that essentially the same volume of non-condensible gases (e.g. oxygen, nitrogen, carbon dioxide, carbon monoxide, etc.) is passed in series through the two reactors with the effluent from the second reactor having substantially only an increased content of maleic anhydride. The non-condensible gases are fed to the first reactor as air and change in composition but not substantially in volume during passage through the reactors.

The catalyst which is suitably used in forming the catalyst beds for carrying out the above-described oxidations can be any of the vanadium-molybdenum contact catalysts used in the benzene oxidation art and the invention is in no way limited to any particular catalyst. Particularly advantageous catalysts are those described in Barker U.S. Pat. No. 3,759,840 dated Sept. 18, 1973. Also suitable are the catalysts described in Barker U.S. application Ser. No. 300,026 filed Oct. 24, 1972 (Now U.S. Pat. No. 3,838,067) which involve the inclusion of manganese, tin, tungsten and/or bismuth values in the catalysts of U.S. Pat. No. 3,759,840 in the amount of 0.005 to 0.1 mol per mol of V. Said U.S. Pat. No. 3,759,840 and said application Ser. No. 300,026 are incorporated herein by reference.

The process of the invention is readily carried out in conventional oxidation reactors or converters and such apparatus forms no part of the invention. One type of such reactor is described, for example, in Jaeger U.S. Pat. No. 1,812,341 dated June 30, 1931. Another type of reactor is described in Lidov U.S. Pat. No. 3,247,279 dated Apr. 19, 1966. Said Jaeger and Lidov patents are incorporated herein by reference merely by way of illustration.

Following the oxidation reactions, the effluent from the second reactor with its relatively high content of maleic anhydride is processed in conventional manner, including a first condensation in which a major proportion of the maleic anhydride vapor is condensed to produce a body of liquid maleic anhydride, and the remaining gaseous stream is then absorbed in water to produce an aqueous maleic acid solution which is subsequently dehydrated in conventional manner, and the recovered maleic anhydride is subjected to any desired purification, also in conventional manner. As mentioned, it is a feature of the invention that the volume of non-condensible gases flowing from the two reactors is substantially the same as the volume of non-condensible gases which would flow from a single reactor, so that the downstream process equipment for a single reactor system will readily handle the effluent from the multiple reactor system of this invention. Obviously, minor changes in the volume of gases can be made without departing from the invention, e.g. small amounts of the gases can be added or withdrawn, if desired. The maleic anhydride condenser is operated to condense the normal amount of maleic anhydride plus all of the additional maleic anhydride which can be produced in accordance with the process of this invention, so that the gaseous stream issuing from the condenser will contain essentially no more uncondensed maleic anhydride than the corresponding stream from a single reactor system, and will impose essentially no additional burden on the downstream processing equipment except, of course, on any optional final purification equipment which may be employed to provide maleic anhydride of desired purity. The specific treatments of the second reactor effluent form no part of the invention and are carried out in conventional manner in conventional equipment, which also forms no part part of the invention. By way of illustration, however, a representative maleic anhydride separation system is described, for example, in Feder U.S. Pat. No. 3,054,806 dated Sept. 18, 1962, and a representative maleic acid dehydration system is described in Ohsol et al. U.S. Pat. No. 2,729,599 dated Jan. 3, 1956. Said Feder and Ohsol et al. patents are incorporated herein by reference.

By operating in accordance with the above-described process parameters which characterize the process of this invention, it is possible substantially to double or even further increase the productivity of a maleic anhydride producing plant by adding essentially only a second oxidation unit and appropriate relatively minor auxilliary equipment; e.g. to provide the desired pressures and to permit the introduction of benzene, preferably in vaporized form, between the oxidation zones. The remainder of the plant can remain substantially unchanged. Typically, productivity increases of 60 to 150% are readily obtained.

The features of the invention will be more readily apparent from the following specific examples of typical application. It will be understood, however, that these examples are for the purpose of illustration only and are not to be interpreted as limiting the invention.

EXAMPLE I

A catalyst is produced by the following procedure. A first solution (A) is prepared by dissolving 175 g. ammonium metavanadate slowly with stirring in 500 ml. of conc. hydrochloric acid (sp. g. 1.19) followed by the addition of 9.8 g/ manganese nitrate in the form of a 50% solution in water (25° C.). A second solution (B) is prepared by dissolving 100 g. of ammonium paramolybdate in 500 ml. of conc. hydrochloric acid, and 3 g. sodium stannate and 9 g. iron nitrate in hot water (75° C.) are added to the solution with stirring, followed by the addition of a mixture of 10.5 g. disodium acid phosphate dodecahydrate and 9.6 g. sodium borate pentahydrate dissolved in 75 ml. hot water (70° C.). Solution B is then slowly added to solution A with stirring and the resultant mixture poured over 1500 ml. of 3-5 mesh aggregate pellets of a commercial alumina catalyst carrier composed of about 85% $Al_2O_3$, about 13.5% $SiO_2$, and very small amounts of other oxides as impurities, primarily alkali metal oxides and alkaline earth metal oxides. This carrier has an apparent porosity of about 55-60%, a surface area of about 0.1 sq. meters per gram and a pore diameter range of about 95% of 50-1500 micron size. The mixture is heated in a rotating glass jar to evaporate the solution to dryness, leaving a greenish coated product which is then placed in an activation oven for four hours at 400° C. to activate it, the additive elements thereby being converted into their oxides.

The oxidizing apparatus consists of two reactors, each containing a catalyst tube made of 1 in. outside diameter 14 BWG carbon steel having a length of 144 in. The first reactor is provided with a single salt bath and the second reactor is provided with two separate salt baths, all of the baths being contained in suitable jackets surrounding the reactor tubes. A jacketed line connects the outlet of the first reactor tube with the inlet of the second reactor tube. In this line, there is provided an inlet for injection of controlled amounts of vaporized benzene. Thus, the gas flow system is constructed so that the total effluent from the first reactor is fed without cooling into the second reactor, after introduction of a controlled amount of benzene. The first reactor tube is filled with a 10.5 foot bed of the catalyst prepared as described above, and a 1 foot section of inert support (used to make the catalyst) at the gas inlet and serves as a preheater. The inlet-end portion of the second reactor is provided with a 3.0 foot bed of catalyst whereas the outlet-end portion of the second reactor contains a 7.5 foot bed of catalyst for a total bed equal in height to the catalyst bed of the first reactor, with a 1 foot secton of inert support serving as a preheater.

Oxidations under various temperature conditions using various concentrations of benzene were then carried out in this oxidizing apparatus. In each case, a space velocity of 2500 hrs. $^{-1}$ (standard conditions) was maintained and there was an inlet pressure into the first reactor of 28 psig and an outlet pressure from the first reactor of 21.3 psig and in the second reactor an inlet pressure of 17 psig and an outlet pressure of 7.2 psig. The following table gives the pertinent data for these oxidations, showing in each case, the length of the run, the temperatures in the first reactor and in each of the two portions of the second reactor, the benzene concentration (mol percent) at the inlet and at the outlet of each of the reactors, together with the selectivity, the conversions and the yields observed in No. 1 reactor, as well as with these values for the overall oxidation. In the table, the temperatures are those of the surrounding salt baths. T indicates the temperature in the first reactor, $T_2$ the temperature in the upstream portion of the second reactor and $T_3$ the temperature in the downstream portion of the second reactor. The selectivities, conversions and yields are calculated as follows:

$$\text{Conversion (\%)} = \frac{\text{weight benzene reacted}}{\text{weight benzene fed}} \times 100$$

$$\text{Selectivity (\%)} = \frac{\text{mols maleic anhydride produced}}{\text{mols benzene reacted}} \times 100$$

$$\text{Yield (\%)} = \frac{\text{weight maleic anhydride produced}}{\text{weight benzene fed}} \times 100$$

The column "Benz. in" for Reactor No. 2 shows the mol. percent of benzene in the gas entering Reactor No. 2 after benzene has been added to the gas exiting the first reactor and already containing the benzene shown as "Benz. out" for Reactor No. 1.

TABLE I

| Run No. | Time, hr. | Reactor No. 1 ||||| Reactor No. 2 |||||||
|---|---|---|---|---|---|---|---|---|---|---|---|---|---|
| | | T | Benz. in | Benz. out | Selec. | Conv. | Yield | $T_2$ | $T_3$ | Benz. in | Benz. out | Overall Selec. | Conv. | Yield |
| 1 | 10 | 349 | 1.359 | .063 | 71.2 | 95.5 | 85.5 | 349 | 349 | 1.370 | .128 | 68.9 | 95.3 | 82.4 |
| 2 | 44 | 348 | 1.353 | .063 | 71.6 | 95.5 | 86.0 | 349 | 361 | 1.376 | .075 | 69.8 | 97.4 | 85.4 |
| 3 | 14 | 346 | 1.359 | .067 | 71.4 | 95.4 | 85.5 | 349 | 370 | 1.332 | .027 | 67.6 | 99.3 | 84.3 |
| 4 | 27 | 346 | 1.363 | .061 | 71.5 | 95.7 | 85.8 | 349 | 371 | 1.376 | .039 | 65.8 | 98.6 | 81.5 |
| 5 | 11 | 346 | 1.365 | .069 | 71.2 | 95.2 | 85.1 | 350 | 350 | 1.362 | .137 | 68.7 | 95.3 | 82.2 |

TABLE I-continued

| Run No. | Time, hr. | Reactor No. 1 | | | | | | Reactor No. 2 | | | | Overall | | |
|---|---|---|---|---|---|---|---|---|---|---|---|---|---|---|
| | | T | Benz. in | Benz. out | Selec. | Conv. | Yield | $T_2$ | $T_3$ | Benz. in | Benz. out | Selec. | Conv. | Yield |
| 6 | 32 | 346 | 1.338 | .066 | 71.3 | 95.3 | 85.4 | 355 | 355 | 1.339 | .092 | 68.8 | 96.5 | 83.4 |
| 7 | 34 | 349 | 1.338 | .064 | 72.7 | 95.3 | 87.1 | 357 | 366 | 1.338 | .054 | 68.3 | 97.9 | 83.7 |
| 8 | 6 | 348 | 1.338 | .061 | 72.3 | 95.5 | 86.8 | 350 | 350 | 1.323 | .119 | 68.6 | 95.5 | 82.1 |
| 9 | 8 | 349 | 1.485 | .070 | 72.5 | 95.5 | 87.1 | 352 | 352 | 1.317 | .143 | 69.1 | 95.0 | 82.6 |
| 10 | 10 | 349 | 1.475 | .068 | 72.4 | 95.6 | 87.0 | 352 | 352 | 1.519 | .145 | 68.6 | 95.6 | 82.4 |
| 11 | 15 | 351 | 1.356 | .065 | 73.4 | 95.4 | 87.9 | 351 | 351 | 1.342 | .138 | 70.7 | 95.0 | 84.4 |
| 12 | 15 | 349 | 1.345 | .070 | 72.7 | 95.1 | 86.8 | 352 | 361 | 1.311 | .074 | 70.8 | 97.2 | 86.4 |
| 13 | 69 | 348 | 1.500 | .073 | 71.2 | 95.4 | 85.5 | 353 | 353 | 1.539 | .140 | 70.0 | 95.4 | 83.9 |
| 14 | 208 | 347 | 1.504 | .070 | 71.5 | 95.5 | 85.7 | 353 | 361 | 1.505 | .078 | 68.7 | 97.4 | 84.0 |
| 15 | 54 | 347 | 1.341 | .067 | 71.6 | 95.2 | 85.7 | 352 | 352 | 1.327 | .115 | 69.4 | 95.6 | 83.1 |
| 16 | 100 | 350 | 1.529 | .073 | 71.3 | 95.4 | 85.4 | 351 | 351 | 1.343 | .128 | 69.3 | 95.5 | 83.2 |
| 17 | 53 | 351 | 1.506 | .071 | 71.7 | 95.4 | 86.0 | 351 | 362 | 1.357 | .081 | 68.3 | 97.4 | 83.7 |
| 18 | 39 | 351 | 1.488 | .071 | 71.5 | 95.5 | 85.7 | 351 | 363 | 1.317 | .066 | 68.7 | 97.6 | 84.2 |
| 19 | 47 | 351 | 1.505 | .068 | 71.5 | 95.6 | 85.9 | 351 | 364 | 1.330 | .058 | 68.3 | 97.9 | 84.0 |
| 20 | 46 | 352 | 1.514 | .066 | 71.2 | 95.7 | 85.6 | 351 | 365 | 1.333 | .053 | 68.2 | 98.2 | 84.1 |
| 21 | 40 | 350 | 1.475 | .068 | 71.9 | 95.5 | 86.5 | 351 | 365 | 1.320 | .040 | 68.1 | 98.7 | 84.4 |
| 22 | 36 | 350 | 1.492 | .063 | 71.7 | 95.9 | 86.3 | 351 | 367 | 1.329 | .039 | 68.2 | 98.6 | 84.5 |
| 23 | 75 | 347 | 1.497 | .067 | 71.5 | 95.6 | 86.0 | 351 | 368 | 1.319 | .032 | 67.6 | 98.9 | 84.0 |
| 24 | 62 | 347 | 1.485 | .065 | 71.2 | 95.7 | 85.6 | 351 | 369 | 1.349 | .022 | 67.5 | 99.3 | 84.2 |
| 25 | 36 | 347 | 1.510 | .070 | 71.3 | 95.5 | 85.5 | 351 | 370 | 1.355 | .021 | 67.2 | 99.4 | 83.8 |
| 26 | 17 | 347 | 1.335 | .064 | 71.3 | 95.4 | 85.5 | 344 | 344 | 1.340 | .119 | 69.9 | 95.3 | 83.6 |

The foregoing oxidation runs each resulted, as is apparent from the data presented, in a substantial increase in the productivity of the oxidation step. No increase in the ratio of color-producing by-products, which are generally of an aldehydic nature, was observed, and the color of the product in aqueous solution was comparable to maleic anhydride produced in conventional single reactor operation. This observation was surprising because it could have been expected that the oxidation carried on in the second reactor, which was under conditions of lower oxygen partial pressures than existed in the first reactor, would lead to less complete oxidation with increased formation of color producing bodies.

What is claimed is:

1. A process for producing maleic anhydride which comprises oxidizing benzene with molecular oxygen in a first oxidation zone, in the presence of a catalyst comprising vanadium and molybdenum, said benzene being introduced into said zone as a vapor in admixture with air in a concentration of about 1 to 2 mol percent, withdrawing a gaseous stream from the outlet of said zone, and without cooling said gaseous stream, introducing substantially only benzene into said stream to provide a benzene concentration of about 0.8 to 1.8 mol percent in said withdrawn stream, and introducing the resulting benzene-enriched stream into a second oxidation zone containing a catalyst comprising vanadium and molybdenum to oxidize the benzene in said stream with the molecular oxygen in said stream, said first oxidation zone being at a temperature within the range of 330° –425° C., said second oxidation zone being substantially at least at the temperature of said first oxidation zone and the gaseous feed to the first oxidation zone being at a pressure of 10–60 psig and being caused to flow at a space velocity of 1800 to 3500 hr.$^{-1}$ 2. A process as defined in claim 1, wherein said second zone is maintained at two different temperatures, the temperature of the downstream portion of the second zone being greater than the temperature of the upstream portion of said second zone.

3. A process for producing maleic anhydride which comprises oxidizing benzene with molecular oxygen in a first oxidation zone, in the presence of a catalyst comprising vanadium and molybdenum, said benzene being introduced into said zone as a vapor in admixture with air in a concentration of about 1 to 2 mol percent, withdrawing a gaseous stream from the outlet of said zone, and without cooling said gaseous stream, introducing substantially only benzene into said stream to provide a benzene concentration of about 0.8 to 1.8 mol percent in said withdrawn stream, and introducing the resulting benzene-enriched stream into a second oxidation zone containing a catalyst comprising vanadium and molybdenum to oxidize the benzene in said stream with a molecular oxygen in said stream, said benzene-enriched stream being substantially at the temperature of said withdrawn stream, said first oxidation zone being at a temperature within the range of 330° –425° C., said second oxidation zone being at a higher temperature than the temperature of said first oxidation zone, and the gaseous feed to the first oxidation zone being at a pressure of 10–60 psig and being caused to flow at a space velocity of 1800 to 3500 hr.$^{-1}$, wherein the ratio of color-producing by-products in the gases leaving the second reaction zone is substantially no greater than the ratio of color-producing by-products in said gaseous stream leaving the first reaction zone.

4. A process as defined in claim 3, wherein said second zone is maintained at two different temperatures, the temperature of the downstream portion of the second zone being greater than the temperature of the upstream portion of said second zone.

* * * * *